United States Patent
Bak et al.

(10) Patent No.: US 9,215,851 B2
(45) Date of Patent: Dec. 22, 2015

(54) *GUZMANIA* PLANT NAMED 'ROSTARA'

(71) Applicants: Elly Bak, Rijsenhout (NL); Nicolaas Steur, Oude Niedorp (NL)

(72) Inventors: Elly Bak, Rijsenhout (NL); Nicolaas Steur, Oude Niedorp (NL)

(73) Assignee: Corn Bak B.V. (NL)

(*) Notice: Subject to any disclaimer, the term of this patent is extended or adjusted under 35 U.S.C. 154(b) by 0 days.

(21) Appl. No.: 14/278,422

(22) Filed: May 15, 2014

(65) Prior Publication Data

US 2015/0327454 A1  Nov. 19, 2015

(51) Int. Cl.
*A01H 5/02* (2006.01)
*A01H 5/10* (2006.01)
*A01H 1/02* (2006.01)

(52) U.S. Cl.
CPC ... *A01H 5/02* (2013.01); *A01H 1/02* (2013.01)

(58) Field of Classification Search
USPC .......................................................... Plt./371
See application file for complete search history.

(56) References Cited

U.S. PATENT DOCUMENTS

PP7,471 P  *  3/1991  Bak et al.

* cited by examiner

*Primary Examiner* — David H Kruse
(74) *Attorney, Agent, or Firm* — Cassandra Bright

(57) ABSTRACT

A new and distinct *Guzmania* hybrid named 'ROSTARA' characterized by solid growth habit; funnel-form rosette plant, measuring about 55 cm in height (above the pot when flowering); numerous, green color foliage (measuring about 40-55 cm length and about 3-4.5 cm in width) Superior floral bract production; primary bracts are red in color (closest to RHS 46A) compound inflorescence, measuring about 22 cm in height and about 22 cm in diameter and long lasting habit.

3 Claims, 2 Drawing Sheets
(2 of 2 Drawing Sheet(s) Filed in Color)

GUZMANIA PLANT NAMED 'ROSTARA'

FIELD OF THE INVENTION

The present invention relates to a new, distinct and stable hybrid of *Guzmania* hybrid, hereinafter referred to as 'ROSTARA'. The present invention relates to seeds which are the *Guzmania* hybrid 'ROSTARA', as well as, plants and plant parts produced by these seeds which have all of the morphological and physiological characteristics of the *Guzmania* hybrid 'ROSTARA'. The present invention also relates to methods for producing these seeds and plants of the *Guzmania* hybrid 'ROSTARA'. Furthermore, the present invention relates to a method of producing progeny *Guzmania* plants by crossing *Guzmania* 'ROSTARA', as either the female or seed or male or pollen parent, with another *Guzmania* plant and selecting progeny.

BACKGROUND OF THE INVENTION

The present invention relates to a new, distinct and stable hybrid of *Guzmania* hybrid, and hereinafter referred to by the variety denomination 'ROSTARA'. The new *Guzmania* 'ROSTARA' originated from a cross made in a controlled breeding program by the inventors in 2009, and then first flowered in 2012, in Assendelft, The Netherlands. The female or seed parent is the *Guzmania lingulata* inbred line identified by code 12039768 (unpatented). The male or pollen parent is the *Guzmania wittmackii* inbred line identified by code 12039788 (unpatented).

*Guzmania* is a member of the Bromeliaceae family. *Guzmania* is predominantly epiphytic with a few terrestrial species and is native to the tropics. For the most part, species vary in diameter from 7 or 8 inches to 3 or 4 feet and have rosettes of glossy, smooth-edged leaves.

Floral bracts of *Guzmania* frequently have brilliant colors and may last for many months. The range of colors for *Guzmania* is generally from yellow through orange but may also include flame red and red-purple. White or yellow, tubular, three-petaled flowers may also appear on a stem or within the leaf rosette but are usually short-lived.

*Guzmania* may be advantageously grown as pot plants for greenhouse or home use. Typically, the plants are shaded from direct sunlight. During the spring to autumn period, the central vase-like part of the leaf rosette is normally filled with water.

*Guzmania* is native to tropical America. Leaves of *Guzmania* are usually formed as basal rosettes which are stiff and entire and in several vertical ranks. *Guzmania* plants have terminal spikes or panicles which are often bracted with petals united in a tube about as long as the calyx. The ovary is superior and the seeds plumose.

Asexual propagation of *Guzmania* is frequently performed by vegetative means through the use of tissue culture practices. Propagation of *Guzmania* can also be from offshoots which can be detached from the mother plant and grown in an appropriate soil or bark mixture.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

A *Guzmania* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect their morphological and physiological characteristics.

A need exists for a greater variety of *Guzmania* cultivars with attractive ornamental features. Additionally, a need exists for additional *Guzmania* hybrid cultivars that can be easily propagated by seed. The new *Guzmania* 'ROSTARA' was developed through a controlled breeding program and exhibits unique, desirable and stable characteristics.

SUMMARY OF THE INVENTION

The present invention provides *Guzmania* plant selections that are solid, medium-sized, long-lasting hybrids with superior bract production and red inflorescence that exhibits good keeping quality. The present invention also provides *Guzmania* plant selections with a compound inflorescence with a unique red color which distinguishes the new cultivar from typical *Guzmania*.

These and other objectives have been achieved in accordance with the present invention which provides 'ROSTARA' as a new *Guzmania* cultivar that is a product of a planned breeding program conducted by the inventors, Elly Bak and Nico D. M. Steur, in Assendelft, The Netherlands, in 2009. The female or seed parent is the *Guzmania lingulata* inbred line identified by code 12039768 (unpatented). The male or pollen parent is the *Guzmania wittmackii* inbred line identified by code 12039788 (unpatented).

Both parental cultivars have a sufficient degree of homozygosity such that the progeny of the cross are genetypically and phenotypically uniform. The new hybrid 'ROSTARA' therefore can be produced by sexual reproduction by crossing the parental inbred lines identified by the codes 12039768 and 12039788 to produce a population of progeny plants, each of which has the combination of characteristics as herein disclosed for the new hybrid 'ROSTARA'.

At least 2500 seeds of the *Guzmania* hybrid 'Rostara' were deposited on Aug. 12, 2014, at the American Type Culture Collection (ATCC), 10801 University Blvd., Manassas, Va., a Budapest Treaty recognized depository which affords permanence of the deposit, and accorded ATCC Accession No. PTA-121481.

OBJECTS OF THE INVENTION

The present invention relates to seeds which produce *Guzmania* hybrid 'ROSTARA'. The present invention also relates to *Guzmania* plants, and parts thereof; having all the physiological and morphological characteristics of *Guzmania* hybrid 'ROSTARA'. The present invention relates to a plant produced from seeds which are *Guzmania* hybrid 'ROSTARA'. The present invention also relates to plant parts, such as pollen, seeds or inflorescence produced by *Guzmania* hybrid 'ROSTARA'.

The present invention relates to a method of producing seed which are *Guzmania* hybrid 'ROSTARA', by a crossing *Guzmania lingulata* inbred line identified by code 12039768 (unpatented) as the female or seed parent with *Guzmania wittmackii* inbred line identified by code 12039788 (unpatented) as the male or pollen parent. harvesting seeds produced from said cross.

The present invention also relates to a method of producing plants having all the physiological and morphological characteristics of the *Guzmania* hybrid 'ROSTARA' comprising the steps of (a) crossing *Guzmania lingulata* inbred identified by code 12039768 (unpatented) as a female or seed parent with *Guzmania wittmackii* inbred line identified by code 12039788 (unpatented) as the male or pollen parent. (b) harvesting seeds produced from said cross; and (c) producing plants from said harvested seeds.

The present invention also relates to producing progeny plants from the cross of *Guzmania* hybrid 'ROSTARA', as the female or male parent, with another *Guzmania* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Guzmania* hybrid 'ROSTARA' showing the colors as true as is reasonably possible with colored reproductions of this type. Colors in the photographs may differ slightly from the color values cited in the detailed botanical description which accurately describes the color of 'ROSTARA'.

DETAILED BOTANICAL DESCRIPTION

Figure 1:
FIG. 1 shows a side view perspective of a typical flowering plant of 'ROSTARA', at 12 months of age from potting size.
Figure 2:
FIG. 2 shows a close-up top view perspective of the inflorescence and top bracts produced by a typical potted, flowering plant of 'ROSTARA', at 12 months of age from potting size.

The present invention was created by the inventors, Elly Bak and Nicolaas D. M. Steur in 2009, and flowered for the first time in 2012 in Assendelft, The Netherlands.

This invention is directed to *Guzmania* plant having all the morphological and physiological characteristics of the hybrid 'ROSTARA' produced from seeds which are the product of the cross of the *Guzmania lingulata* inbred line identified by code 12039768 (unpatented) as the female or seed parent with the *Guzmania wittmackii* inbred line identified by code 12039788 (unpatented) as the male or pollen parent. Both parents have a sufficient degree of homozygosity such that the progeny of the cross were, and continue to be, phenotypically uniform. The new hybrid 'ROSTARA' can therefore be produced by sexual reproduction by crossing of the inbred selections identified by the codes 12039768 and 12039788 to produce a population of progeny plants, each of which has the combination of characteristics herein disclosed for the new hybrid 'ROSTARA'.

The new hybrid 'ROSTARA' can also be produced by asexually reproducing progeny from the cross of the parental inbred lines identified by the codes 12039768 and 12039788. Asexual reproduction of the new cultivar by vegetative means by cuttings was first performed in 2012, in Assendelft, The Netherlands. The first 'ROSTARA' plants propagated through the use of such cuttings flowered in 2014, in Assendelft, The Netherlands, and have demonstrated that the new cultivar reproduces true-to-type and that the combination of characteristics as herein disclosed for the new cultivar are firmly fixed and retained through successive generations of asexual reproduction.

The following traits have been repeatedly observed and are determined to be unique characteristics of 'ROSTARA' which in combination distinguish this *Guzmania* as a new and distinct cultivar:

1. Stemless growth habit;
2. Funnel-form rosette plant, measuring about 55 cm in height (above the pot when flowering);
3. Numerous, green color foliage (measuring about 50 cm in length and about 4.5 cm in width.
4. Superior floral bract production;
5. Bracts are red in color (closest to RHS 46A),
6. compound inflorescence, measuring about 22 cm in height, when flowering and about 22 cm in diameter
7. Long-lasting habit.

Of the many commercial cultivars known to the present inventors, the most similar in comparison to the new *Guzmania* hybrid 'ROSTARA' is the *Guzmania* cultivar 'OSTARA'. Plants of the new hybrid 'ROSTARA' differ from plants of 'OSTARA' primarily in color of the inflorescence. Primary bracts of 'OSTARA' are red closest to RHS 44A. Primary bracts of 'ROSTARA' are darker red, closest to RHS 46A.

'ROSTARA' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photographs, together with the following observations, measurements and values describe the new *Guzmania* 'ROSTARA' as grown in a greenhouse in Assendelft, The Netherlands, under conditions which closely approximate those generally used in commercial practice. Plants of 'ROSTARA' were grown in a greenhouse with day temperatures ranging from 20° C. to 28° C. and night temperatures ranging from 18° C. to 23° C. No artificial lighting or photoperiodic treatments were conducted, but plants of 'ROSTARA' are forced into flowering. The following fertilizer is added when growing plants of 'ROSTARA': 1 part nitrogen, 0.6 parts phosphor, 2 parts Kalium and 0.1 parts magnesium.

Color references are made to the Royal Horticultural Society Colour Chart (RHS), 2001 edition, except where general colors of ordinary significance are used. Color values were taken under daylight conditions in a greenhouse in Assendelft, The Netherlands. The age of the plants of 'ROSTARA' described is about 16 weeks after flowering treatment.

Classification:
Botanical: *Guzmania* sp.
Parentage:
  Female Parent: *Guzmania lingulata* inbred line identified by code 12039768 (unpatented)
  Male Parent: *Guzmania wittmackii* inbred line identified by code 12039788 (unpatented)
Plant:
  General Appearance and Form:
    Height: About 55 cm (when flowering)
    Width: About 70 cm
    Shape: Funnel form rosette
  Growth habit: Stemless
  Plant Vigor: Good
  Flowering Season: A fully grown plant can flower year round, starting 16 weeks after induction of natural light or through flowering treatment. Cold Tolerance: Frost tender. Temperatures below 5° C. may damage plants.
Fragrance: None
Foliage:
 Quantity: About 20 (depending on the size of the plant)
 Size of Leaf:
  Length: About 40 cm to 55 cm (when flowering)
  Width: About 3 to 4.5 cm
 Overall Shape: linear lanceolate
 Apex Shape: Acuminate
 Base Shape: Strap-like around central axis
 Margin: Entire
 Texture: Smooth
 Orientation: Leaf blades arch continuously from base.
 Color: Leaf color can vary somewhat depending on growing conditions.
  Immature and Mature:
   Upper surface: green, RHS 137A
   Under surface: green, RHS 137A with anthocyanin at base
 Venation: None
Inflorescence:
 Borne: Erect stalks
 Shape: Compund
 Size:
  Length: About 22 cm in height when flowering
  Diameter: About 22 cm
 Time of Bloom: A fully grown plant can produce an inflorescence containing about 125 flowers (depending on the size of the plants), and can bloom the whole year starting about 16 weeks after natural induction or through flowering treatment.
 Duration of Bloom: Each flower blooms one (1) day and the total blooming of the whole inflorescence is about 6 weeks.
 Petals:
  Number: 3 per flower
  Length: About 6 cm
  Width: About 0.5 cm
  Overall Shape: Ligulate
  Apex Shape: Obtuse
  Base Shape: Fused
  Color: Upper and under surfaces: yellow, RHS 10B
 Sepals:
  Number: 3 per flower
  Length: About 3 cm
  Width: About 0.5 cm
  Overall Shape: Ligulate
  Apex Shape: Acute
  Base Shape: Fused
  Color: Upper and under surfaces: translucent white, closest to RHS 155D
 Bracts:
 Scape Bracts:
  Quantity: About 9
  Arrangement: Alternate
  Size:
   Length: About 30 cm (lowest) to about 15 cm (scape bracts positioned just below the primary bracts).
   Width: About 4 cm
  Color:
   Upper and under surfaces: lower bracts are green, closest to RHS 137A with red, closest to RHS 46A, changing to red, closest to RHS 46A with a little green, closest to RHS 137A just below the primary bracts.
 Primary Bracts:
  Quantity: About 14
  Arrangement: Alternate
   Size:
    Length: About 15 cm (lowest) to about 8 cm (primary bracts become shorter closer to the top of plant)
    Width: About 3 cm to 4 cm
   Overall shape: recurved and ovate-lanceolate
   Apex shape: Acute
   Base shape: Fused
   Margin: Entire
   Texture: Smooth
   Color:
    Upper and under surfaces: red, RHS 46A
 Floral bracts: enclosed within the inflorescence
 Reproductive Organs:
 Androecium:
 Stamen:
  Number: 6 per flower
  Length: About 5 cm
  Diameter: About 1 mm
  Color: yellow-white, too small to distinguish RHS value
 Anther:
  Length: About 0.6 cm
   Color: yellow-white, too small to distinguish RHS value
 Pollen:
  Amount: None
 Gynoecium:
  Pistil:
   Number: 1 per flower Length: About 4.8 cm
  Stigma:
   Shape: 3-parted
   Width: About 2 mm
    Color: yellow-white, too small to distinguish RHS value
  Style:
   Length: About 4 cm
    Color: yellow-white, too small to distinguish RHS value
  Ovary:
   Position: Superior
   Shape: Conical
   Length: About 0.8 cm
   Diameter: About 0.3 cm
   Color: yellow-green, closest to RHS 150D
SEEDS/FRUIT: sterile hybrid, no seed or fruit produced.
DISEASE/PEST RESISTANCE AND SUSCEPTIBILITY: Neither resistance nor susceptibility to normal diseases and pests of *Guzmania* observed.

We claim:

1. A *Guzmania* plant named 'ROSTARA', representative seed deposited at the American Type Culture Collection (ATCC) having deposit Designation PTA-121481.

2. A *Guzmania* seed deposited at the American Type Culture Collection (ATCC) having deposit Designation PTA-121481.

3. A plant part obtained from the *Guzmania* plant of claim 1.

* * * * *